United States Patent [19]

Failor et al.

[11] Patent Number: 4,882,797
[45] Date of Patent: Nov. 28, 1989

[54] OPHTHALMIC SURGERY STRETCHER

[75] Inventors: Raymond A. Failor; Gerald Peters, both of Seville; Mark Reuter, Chippewa Lake, all of Ohio

[73] Assignee: Hausted, Inc., Medina, Ohio

[21] Appl. No.: 73,677

[22] Filed: Jul. 15, 1987

[51] Int. Cl.[4] .............................................. A61G 7/06
[52] U.S. Cl. .............................................. 5/66; 5/72; 248/118; 269/325; 269/328
[58] Field of Search .................... 5/66, 67, 68, 69, 72; 269/328, 325; 248/118

[56] References Cited

U.S. PATENT DOCUMENTS

| | | | |
|---|---|---|---|
| 1,626,091 | 4/1927 | Macklin | 5/66 X |
| 2,042,399 | 5/1936 | Holme | 269/325 X |
| 3,041,121 | 6/1962 | Comper | 5/66 X |
| 3,411,766 | 11/1968 | Lanigan | 269/325 |
| 3,635,461 | 1/1972 | Bellucci et al. | 5/66 X |
| 3,754,749 | 8/1973 | Lyon et al. | 269/325 |
| 3,929,309 | 12/1975 | De Vore | 248/118 |
| 4,103,170 | 7/1978 | Spradlin | 269/325 X |
| 4,247,091 | 1/1981 | Glowacki et al. | 269/325 |
| 4,390,011 | 6/1983 | Evans | 248/118 X |
| 4,700,691 | 10/1987 | Tari et al. | 269/328 X |

FOREIGN PATENT DOCUMENTS 178046 12/1964 U.S.S.R. ............................ 269/328

OTHER PUBLICATIONS

Hausted Minor Surgery Stretcher 675 Unicare II, (1985).
SurgiBed 962 Stretcher.
Reliance M-701 Stretcher (1985) F and F Koenigkramer, Cincinnati, Oh.
O/E 4000 Stretcher/Table (1985), Lada International, Arlington Heights, Il.

Primary Examiner—Alvin C. Chin-Shue
Assistant Examiner—David L. Talbott
Attorney, Agent, or Firm—Hoffmann & Baron

[57] ABSTRACT

A stretcher is provided which is usable for ophthalmic surgery and other similar operations. It includes a pivotably mounted backrest assembly and a headrest which is pivotably mounted to the backrest assembly. The headrest is substantially narrower in width than the remainder of the stretcher to provide easier access to a patient's head. A receptacle including a locking mechanism is centrally positioned beneath the headrest. It includes a passage which receives the mounting member of a wrist rest assembly or a headrest extension assembly. The headrest extension assembly is mounted to the headrest for providing a full width surface area for the patient's head.

20 Claims, 6 Drawing Sheets

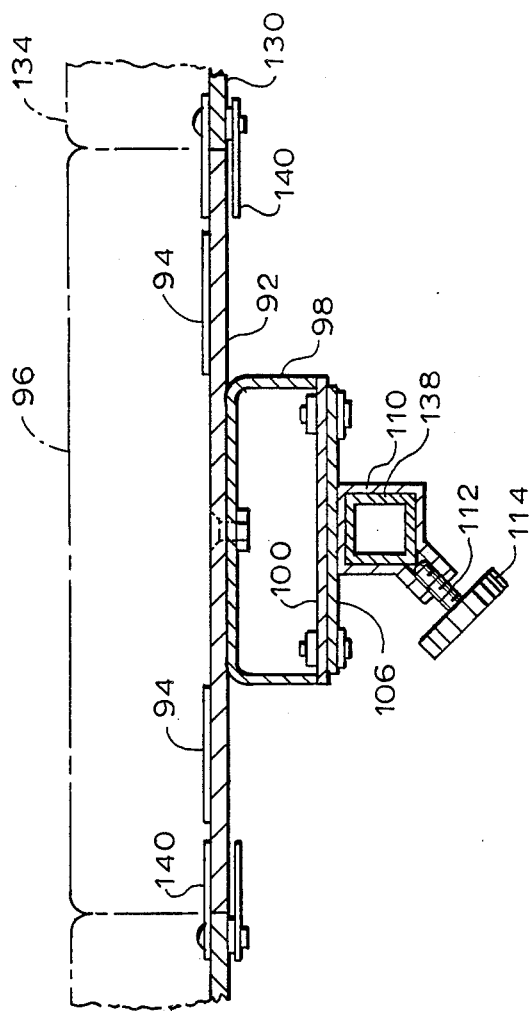

OPHTHALMIC SURGERY STRETCHER

BACKGROUND OF THE INVENTION

1. Field of the Invention.

The field of the invention relates to an ophthalmic surgery stretcher having an articulatable head piece.

2. Brief Description of the Prior Art.

Ophthalmic surgery stretchers typically include a one-piece, tapered fowler/head section, a wrist rest assembly secured to the head end on both sides of the stretcher frame, and controls for adjusting the angular position of the tapered head with respect to the remainder of the stretcher. The fowler/head section is usually adjustable from the flat position through ninety degrees through a single adjustment.

While the tapered head portions of prior art stretchers allow greater access to the patient's head than full width assemblies, the narrow width thereof is disadvantageous once an operation has been completed. Present fowler/head sections also do not allow adjustment of the patient's head to a hyperextended position, and the location of the wrist rests may not permit as close accessability by the physician as may be desired. These factors often increase the time necessary for the physician to complete an operation.

SUMMARY OF THE INVENTION

An ophthalmic surgery support assembly, preferably in the form of a stretcher, is provided by the invention. The stretcher includes a frame, a backrest assembly pivotably mounted to the frame, and a headrest assembly of relatively small width pivotably mounted to the front end of the backrest assembly.

A mounting bracket assembly may be mounted beneath the support surface of the headrest. This assembly is pivotably mounted to the backrest frame. A receiver tube is mounted to the mounting bracket assembly. The tube extends in the longitudinal direction. A wrist rest assembly including an L-shaped support is mounted to the receiver tube when an operation is to be performed. One end of the L-shaped support fits within the tube and is secured therein by a torque knob or the like. The wrist rest assembly may be replaced by a head extension piece which fits about the head support surface and extends the width thereof to substantially the full width of the stretcher. The head extension piece includes a mounting assembly which includes a shaft which fits within the receiver tube.

BRIEF DESCRIPTION OF THE DRAWINGS

FIG. 6 is a sectional elevation view of the head portion of the stretcher including the head extension piece mounted thereto.

DETAILED DESCRIPTION OF THE INVENTION

Figure 1:
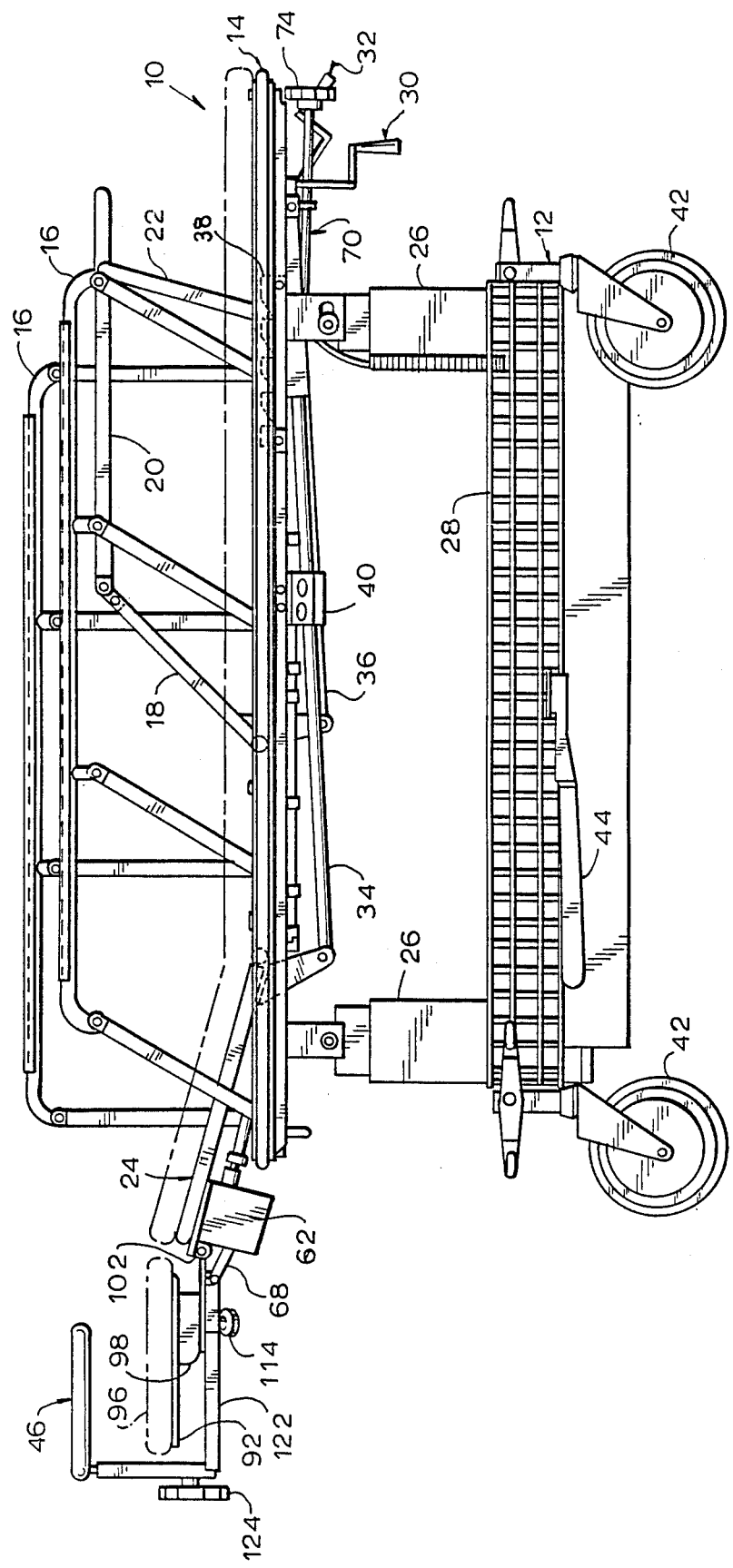
FIG. 1 is a side elevation view of an ophthalmic surgery stretcher in accordance with the invention.
Figure 2:
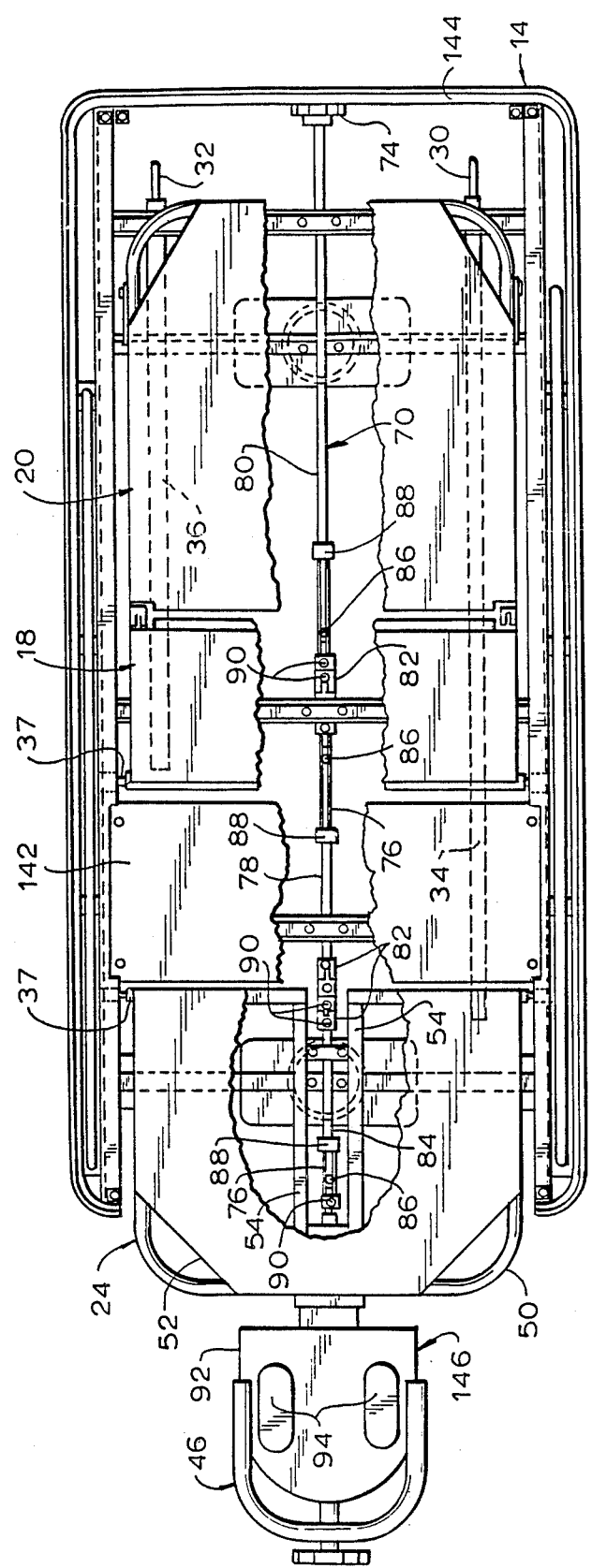
FIG. 2 is a partially cutaway top plan view thereof.

An ophthalmic surgery stretcher 10 according to the invention is shown in FIGS. 1-2. The stretcher includes a base assembly 12, a top assembly 14, a pair of side rails 16, a knee frame and cover assembly 18, a foot frame and cover assembly 20, a foot frame support assembly 22, and a fowler backrest assembly 24. The top assembly is supported by a pair of hydraulic piston/cylinder assemblies 26 mounted to the base assembly. A pair of longitudinal baskets 28 are also mounted to the base assembly.

A pair of elevating screw assemblies including cranks 30,32 are provided for elevating the head and foot ends of the stretcher, respectively. The former includes a relatively long screw nut tube assembly 34 while the latter includes a shorter tube assembly 36. These assemblies allow the crank operated fowler backrest assembly 24 and the knee frame assembly 18 to be raised or lowered. Both the backrest and knee frame assemblies are mounted to pivotable cross bars 37 and rotate about the respective axes of the bars when the appropriate crank is employed. A pair of ratchet plates 38 are provided near the foot end of the stretcher for allowing the foot frame and cover assembly 20 to be positioned at a desired height.

The hydraulic control button assembly 40, wheels 42 including a locking steering caster system, side pedals 44 for adjusting the height of the stretcher, and the components described above have been successfully employed in the industry and their operations are well understood by those skilled in the art. They accordingly shall not be described in greater detail herein.

The invention concerns a novel fowler backrest assembly/headrest combination and a wrist rest assembly 46 and headrest extension assembly 48 which may be employed therewith. The fowler backrest assembly 24 includes a tubular frame 50 made from chrome-plated steel or the like. A steel support plate 52 is mounted to the frame. A pair of parallel, chrome-plated steel tubes 54 are welded to the front and rear portions of the frame 50. A first substantially rectangular steel plate 56 is welded to the opposing tubes 54. The plate 56 supports a gear box 58 including a worm gear reducer 60. A housing 62 may be provided for protecting the gear box and associated components.

A pair of shafts 64 extend in opposite directions from the worm gear reducer and are rotatable therewith. A lever 66 is welded to the end of each shaft. Each lever is pivotably secured to a headrest connecting rod 68.

A linkage assembly 70 having a worm gear 72 on one end thereof and knob 74 at its opposite end is used for actuating the 50:1 ratio gear box 58. The linkage assembly includes a plurality of connecting tubes 76, an extension shaft 78, an adjustment rod 80, a plurality of universal joints 82, and a slide shaft 84. The connecting tubes are hollow and slotted. The shafts extending within these tubes each include a pin 86 near one end thereof which extends through these slots. Rings 88 are provided near each end of the connecting tubes to insure the pins 86 remain within the slots. The length of the linkage assembly may be increased or decreased as the extension shaft 78, adjustment rod 80 and slide shaft 84 move within the respective, slotted connecting tubes 76. The linkage assembly may also be pivoted about the universal joints 82 as the head and foot ends of the stretcher are raised or lowered. Spring pins 90 are employed where appropriate to insure the entire linkage assembly rotates about its longitudinal axis when the knob 74 is turned. Means (not shown) are provided for supporting the linkage assembly at appropriate locations along the stretcher.

Figure 3:
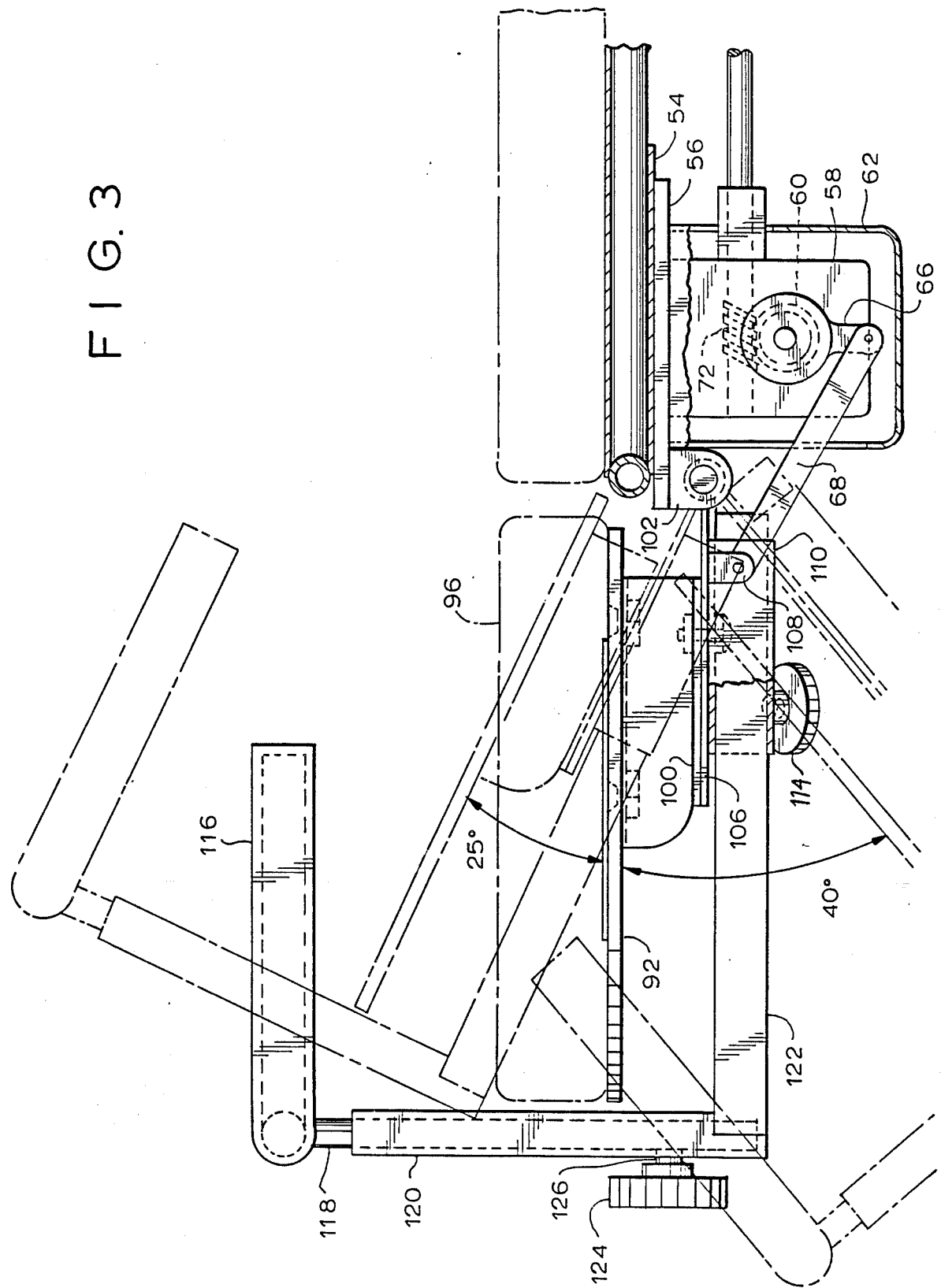
FIG. 3 is an enlarged, partially sectional side elevation view of the head portion of the stretcher.
Figure 4:
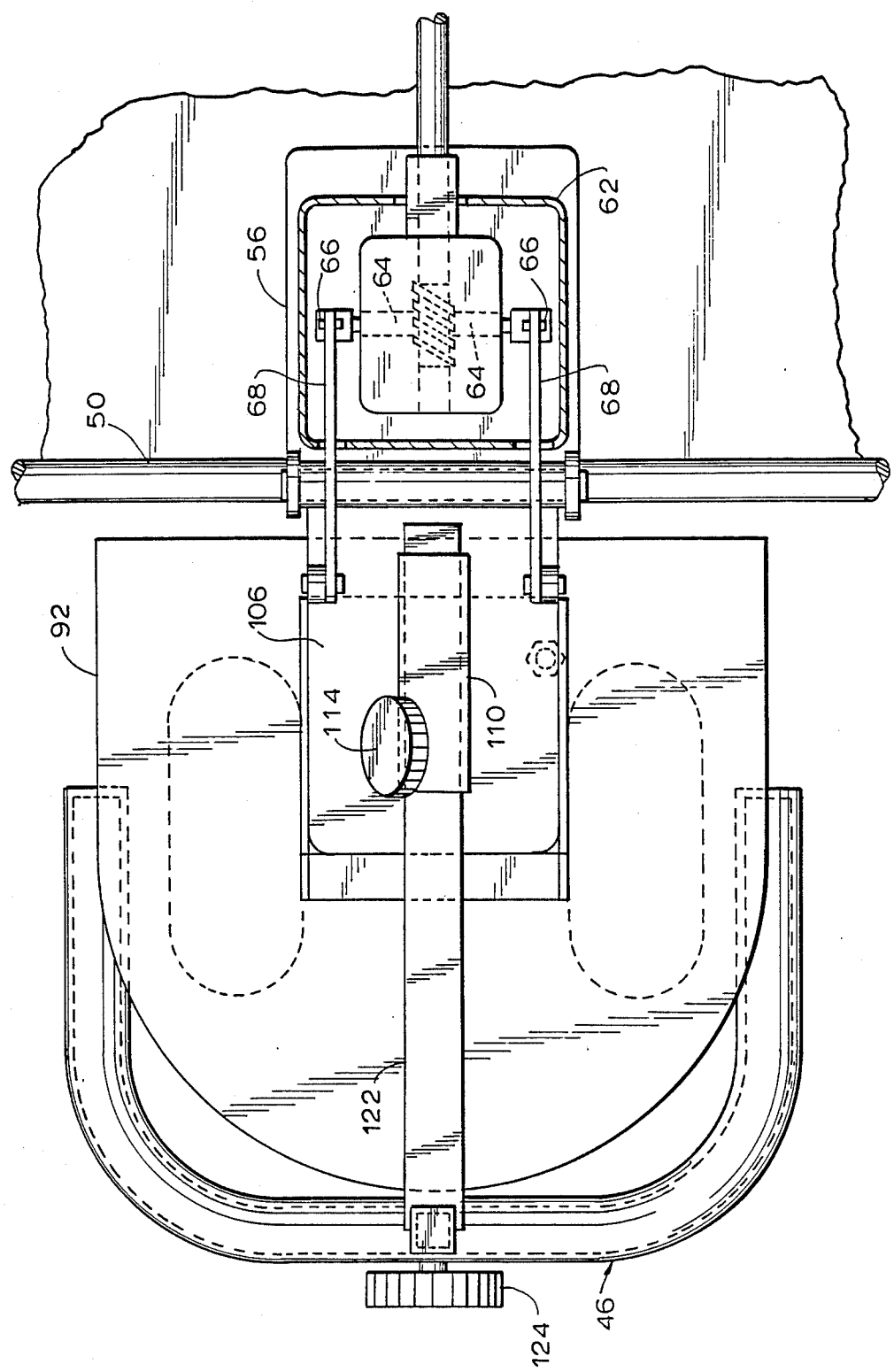
FIG. 4 is an enlarged, partially cutaway bottom plan view of the head portion of the stretcher.

Referring now to FIGS. 3-4, a head support plate 92 is mounted to the fowler backrest assembly 24. A pair of loop fastener sections 94 are adhered to the surface of the plate 92 for allowing a cushion 96 having corresponding hook fastener sections to be secured thereto. The plate is bolted to a bracket 98 which has a cross section resembling an inverted U (see FIG. 6). A base plate 100 is welded to the bracket 98.

A second U-shaped bracket assembly 102 is mounted to the bottom of the rectangular steel plate 56. A rotatable sleeve 104, which runs substantially parallel to the cross bars 37, is supported by the bracket assembly 102. A main support plate 106 is welded at one end to the sleeve 104 and bolted directly beneath the base plate 100. A pair of opposing brackets 108 are welded to the bottom of the main support plate 106. The headrest connecting rods 68 are pivotably mounted, respectively, to the opposing brackets. Rotation of the shafts 64 within the gear box 58 causes the levers 66 to rotate about the axis defined by the shaft. The connecting rods 68, being pivotably secured to the levers 66 and the brackets 108, cause the main support plate 106 to rotate about the longitudinal axis of the sleeve 104 to which it is secured. As shown in FIG. 3, the head support plate 92 is accordingly rotatable with the main support plate 106 to a position about twenty-five degrees above the plane of the fowler backrest assembly to one about forty degrees below it.

A tube 110 having a substantially square cross section is welded to the bottom of the main support plate 106 and extends longitudinally with respect to the stretcher. It is centrally positioned with respect to the sides of the head support plate 92. A set screw 112 and associated knob 114 are mounted to the square tube 110. The wrist rest assembly 46 or the head support extension piece 48 may be mounted to the head piece through the use of the tube.

Referring to FIGS. 3-4, the wrist rest assembly includes a U-shaped wrist support 116, a shaft 118 mounted to the support, a slotted tube 120, and a square tube 122 extending substantially perpendicularly from the slotted tube 120. The square tube 122 is positioned within the slightly larger tube 110 and locked therein by the set screw 112. The height of the wrist support is adjusted by sliding shaft 118 within the slotted tube 120 and securing it with a torque knob 124. The top portion of the wrist rest assembly is locked rotationally in the slotted support tube 120 by a flat washer 126 between the torque knob and the support tube. The washer, when compressed by the torque knob, is loaded against the two edges of the slot (not shown) defined in the support tube, thereby eliminating any rotational movement of the wrist rest assembly.

Figure 5:
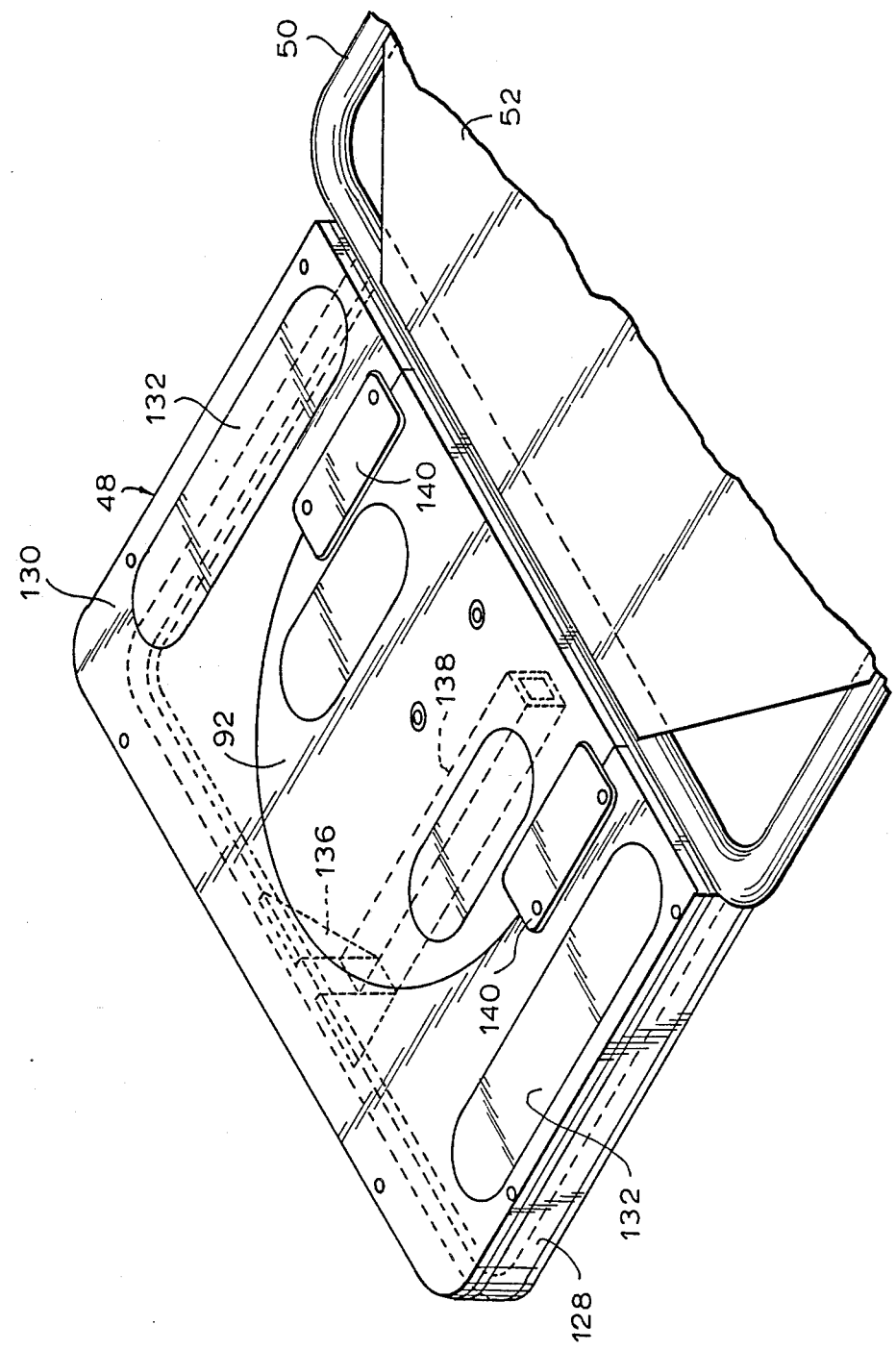
FIG. 5 is a perspective view of the head portion of stretcher including a head extension piece mounted thereto.

The wrist rest assembly 46 must be removed from tube 110 in order to mount the headrest extension assembly 48. As shown in FIGS. 5-6, the headrest extension assembly provides the headrest portion of the stretcher with nearly a full fowler width surface area and a full perimeter protective bumper 128. It includes a generally U-shaped plate 130, a pair of loop fastener sections 132 adhered to the plate, and a generally U-shaped cushion 134 mounted to the plate through the use of hook-type fasteners which adhere to the loop fastener sections. A mounting bracket 136 is secured to the bottom surface of the plate 130 and includes a square tube 138 extending therefrom. This square tube 138 fits within the square tube 110 mounted to plate 106 and is locked therein by the set screw 112. A pair of plates 140 are riveted to opposing edge portions of the plate 130. Each pair defines a slot which accommodates an edge of the head support plate 92.

In use, the backrest assembly 24 is moved to a desired angular orientation by turning crank 30. The knee and foot frame assemblies are likewise positioned by turning crank 32. The seat pan 142 remains in the same plane as the stretcher frame 144 during these operations. If an eye operation is to be conducted, the wrist rest assembly 46 is mounted to the headrest 146 by inserting tube 122 into tube 110. Knob 114 is then turned to lock the wrist rest mounting tube 122 in place. The height of the wrist rest assembly is adjusted by loosening knob 124. This allows the column 118 supporting the wrist support 116 to slide within the slotted tube 120. Once the height has been set, the torque knob is turned to lock the column 118 in position.

The angular orientation of the headrest 146 with respect to the fowler backrest assembly 24 is adjusted by turning knob 74. This causes the linkage assembly 70, and thereby the worm gear 72 to rotate. The worm gear, being engaged to a 50:1 reducer within the gear box 58, causes the rotation of shafts 64 and the levers 66 mounted to the shafts. The connecting rods 68, which are pivotably connected to the levers 66 and the main support plate 106, cause the latter to rotate about the axis of sleeve 104. The headrest assembly 146, being mounted to the main support plate 106, accordingly moves about the longitudinal axis of sleeve 104. Since the sleeve 104 is mounted to the fowler backrest assembly 24, the angular orientation of the headrest assembly may thereby be adjusted with respect to the backrest assembly.

During an operation, the narrow width of the headrest assembly and the convenient location of the wrist rest assembly 46 provide easy access to the patient's head. Once an operation has been completed, the wrist rest assembly is removed by loosening knob 114 and sliding tube 122 out from tube 110. The headrest extension assembly 48 is then mounted to the stretcher by inserting tube 138 within tube 110 and insuring that the head support plate 92 is positioned within the opposing slots defined by the mounting plates 140. The knob 114 is tightened when the cushions 96,134 are in abutting positions. The head support plate 92 and extension plate 130 will also be substantially coplanar and define a substantially contiguous surface area when the headrest extension is properly mounted. A substantially full width headrest is thereby provided which is extremely useful for post-operative recovery.

What is claimed is:
1. A stretcher comprising:
a frame;
a patient support assembly mounted to said frame, said patient support assembly including a backrest assembly;
means for moving said backrest assembly with respect to said frame about a first pivot axis;
a headrest assembly pivotably mounted to said backrest assembly and movable about a second pivot axis which is substantially parallel to said first pivot axis, the width of said headrest assembly being substantially smaller than the width of said back- rest assembly from said second pivot axis to an end of said headrest assembly opposite from said second pivot axis to facilitate a physician's access to a patient's head;

means for moving said headrest assembly with respect to said backrest assembly about said second pivot axis; and means for mounting a wrist rest assembly to said headrest assembly.

2. A stretcher as defined in claim 1 wherein said headrest assembly includes a receptacle having an elongate passage, and locking means mounted to said receptacle for locking a member which may be inserted within said passage.

3. A stretcher as defined in claim 2 wherein said receptacle is a substantially rectangular tube and said locking means includes a set screw mounted to said tube.

4. A stretcher as defined in claim 3 including a wrist rest assembly, said wrist rest assembly including a mounting tube positioned within said elongate passage.

5. A stretcher as defined in claim 3 wherein said headrest assembly includes a head support plate, said receptacle being mounted to said headrest assembly beneath said support plate.

6. A stretcher as defined in claim 1 wherein said headrest assembly includes a pair of substantially parallel longitudinal sides.

7. A stretcher as defined in claim 1 wherein said headrest assembly includes a head support plate having a front end, a rear end, and a pair of sides, a receptacle mounted beneath said head support plate, said receptacle including a passage running substantially perpendicularly to said first and second pivot axes, said passage being centrally positioned with respect to the sides of said head support plate.

8. A stretcher as defined in claim 7 including a wrist rest assembly comprising a wrist support positioned above said head support plate, a mounting member positioned within said passage, and an extensible connecting member positioned adjacent said front end of said head support plate, said connecting member connecting said wrist support and said mounting member and extending substantially perpendicularly with respect to said mounting member.

9. A stretcher as defined in claim 1 wherein said headrest assembly includes a head support plate; said backrest assembly includes a frame assembly, a gear box mounted to said frame assembly and including a rotatable shaft, a pivotable member mounted to said frame assembly, a main support plate secured to said pivotable member, and means for connecting said rotatable shaft of said gear box with said main support plate.

10. A stretcher as defined in claim 9 including a receptacle having a longitudinal passage mounted to said main support plate, said receptacle being positioned beneath said main support plate, said passage running substantially perpendicular to said pivotable member.

11. A stretcher as defined in claim 9 wherein said pivotable member is pivotable about said second pivot axis.

12. A stretcher as defined in claim 1 wherein said headrest assembly includes a pair of substantially parallel, straight sides, a substantially straight rear end, and an arcuate front end.

13. A stretcher comprising:
a frame;
a patient support assembly mounted to said frame, said patient support assembly including a headrest having a substantially narrower width than the remainder of said patient support assembly;
a headrest extension assembly including a recess therein, said headrest positioned within said recess, said headrest and headrest extension defining a substantially coplanar and contiguous support surface of substantially the same width as the remainder of said patient support assembly; and
means for removably mounting said headrest extension assembly to said headrest.

14. A stretcher as defined in claim 13 including a backrest assembly pivotably mounted to said frame, said headrest being pivotably mounted to said backrest assembly.

15. A stretcher as defined in claim 13 wherein said headrest includes a first head support plate and a substantially rectangular receptacle mounted beneath said first head support plate; said headrest extension includes a second head support plate which is substantially coplanar with said first head support plate and a mounting member secured to said second head support plate and extending beneath said second head support plate, said mounting member including a substantially rectangular cross section and being positioned within said receptacle.

16. A stretcher comprising:
a frame;
a patient support assembly mounted to said frame, said patient support assembly including a headrest having a pair of longitudinal sides;
a receptacle mounted beneath said headrest, said receptacle including an elongate passage extending substantially longitudinally with respect to said frame and being substantially centrally located with respect to said longitudinal sides of said headrest;
a wrist rest assembly comprising a wrist support positioned above said headrest, a mounting member positioned within said passage, and a connecting member connecting said wrist support and said mounting member;
means for adjusting the length of said connecting member; and
means for locking said mounting member within said passage.

17. A stretcher as defined in claim 16 wherein said connecting member includes a slotted support tube secured to said mounting member, a shaft positioned within said slotted tube and secured to said wrist support, and means for locking said shaft within said slotted tube.

18. A stretcher as defined in claim 17 wherein said mounting member and passage are substantially rectangular in cross section.

19. A stretcher as defined in claim 16 wherein said patient support assembly includes a backrest assembly pivotably mounted to said frame, said headrest being pivotably mounted to said backrest assembly.

20. A stretcher comprising:
a frame;
a patient support assembly mounted to said frame, said patient support assembly including a backrest assembly;
means for moving said backrest assembly with respect to said frame about a first pivot axis;

a headrest assembly pivotably mounted to said backrest assembly, the width of said headrest assembly being substantially smaller than the width of said backrest assembly to facilitate a physician's access to a patient's head;

means for moving said headrest assembly with respect to said backrest assembly about a second pivot axis which is substantially parallel to said first pivot axis;

means for mounting a wrist rest assembly to said headrest assembly, and a headrest extension removably mounted to said headrest assembly, said headrest extension including a head support surface including a recess defined therein, said headrest assembly being positioned within said recess, said headrest assembly and said head support surface defining a substantially coplanar surface.

* * * * *